(12) United States Patent
Stecco et al.

(10) Patent No.: US 11,813,010 B2
(45) Date of Patent: Nov. 14, 2023

(54) ANCHORS AND TENSIONER AND ANCHOR LOADING SYSTEMS FOR ACTIVE BONE AND JOINT STABILIZATION DEVICES

(71) Applicant: MEDEON BIODESIGN, INC., Taipei (TW)

(72) Inventors: Kathryn A. Stecco, San Jose, CA (US); Carlos Castro, San Jose, CA (US); Stephen Powelson, San Jose, CA (US); Forrest Grinstead, Sunnyvale, CA (US); Damon Covell Campbell, Pacific Grove, CA (US)

(73) Assignee: MEDEON BIODESIGN, INC., Taipei (TW)

(*) Notice: Subject to any disclaimer, the term of this patent is extended or adjusted under 35 U.S.C. 154(b) by 265 days.

(21) Appl. No.: 17/015,991

(22) Filed: Sep. 9, 2020

(65) Prior Publication Data

US 2021/0068879 A1 Mar. 11, 2021

Related U.S. Application Data

(60) Provisional application No. 62/897,832, filed on Sep. 9, 2019.

(51) Int. Cl.
*A61B 17/88* (2006.01)
*A61B 17/68* (2006.01)
(Continued)

(52) U.S. Cl.
CPC ........ *A61B 17/8869* (2013.01); *A61B 17/683* (2013.01); *A61B 17/842* (2013.01);
(Continued)

(58) Field of Classification Search
CPC ........ A61B 17/0401; A61B 2017/0404; A61B 2017/0406; A61B 2017/0409;
(Continued)

(56) References Cited

U.S. PATENT DOCUMENTS

| | | |
|---|---|---|
| 4,959,064 A | 9/1990 | Engelhardt |
| 6,656,184 B1 | 12/2003 | White et al. |

(Continued)

FOREIGN PATENT DOCUMENTS

| | | | | |
|---|---|---|---|---|
| FR | 2906704 A1 | 10/2006 | | |
| FR | 2906704 A1 * | 4/2008 | ......... | A61B 17/7053 |

(Continued)

OTHER PUBLICATIONS

"PCT Search Report and Written Opinion, PCT/US2020/049960", dated Nov. 30, 2020, 12 pages.

*Primary Examiner* — Larry E Waggle, Jr.
(74) *Attorney, Agent, or Firm* — Kurt T. Mulville; VLP Law Group LLP

(57) ABSTRACT

Implant tensioning and/or implant anchor deployment devices are described. Certain embodiments may be recognized in the form of a so-called tensioning "gun." Other embodiments take a simpler and more compact form. Various optional features are described in connection with these embodiments. Optional aspects of anchor embodiments for the subject implants are also described. Some of these features are coordinated for use with the implant tensioning and anchor deployment instrument, others are not.

22 Claims, 11 Drawing Sheets

(51) Int. Cl.
*A61B 17/56* (2006.01)
*A61B 17/04* (2006.01)
*A61B 17/84* (2006.01)

(52) U.S. Cl.
CPC .. *A61B 17/8872* (2013.01); *A61B 2017/0404* (2013.01); *A61B 2017/0409* (2013.01); *A61B 2017/564* (2013.01); *A61B 2017/681* (2013.01)

(58) Field of Classification Search
CPC ........ A61B 2017/564; A61B 2017/681; A61B 17/683; A61B 17/842; A61B 17/88; A61B 17/8869; A61B 17/8872
See application file for complete search history.

(56) References Cited

U.S. PATENT DOCUMENTS

| | | | |
|---|---|---|---|
| 7,235,091 B2 | 6/2007 | Thornes | |
| 7,422,037 B2 | 9/2008 | Levin et al. | |
| 7,833,256 B2 | 11/2010 | Biedermann et al. | |
| 7,875,057 B2 | 1/2011 | Cook et al. | |
| 7,985,222 B2 | 7/2011 | Gall et al. | |
| 8,048,134 B2 | 11/2011 | Partin | |
| 8,348,960 B2 | 1/2013 | Michel et al. | |
| 8,449,574 B2 | 5/2013 | Biedermann et al. | |
| 8,491,583 B2 | 7/2013 | Gall et al. | |
| 9,084,644 B2 | 7/2015 | Knueppel | |
| 10,052,143 B2 | 8/2018 | Hulliger | |
| 10,194,946 B2 | 2/2019 | Stecco et al. | |
| 10,259,604 B2 | 4/2019 | Myers | |
| 10,555,766 B2 | 2/2020 | Stecco et al. | |
| 2006/0264954 A1 | 11/2006 | Sweeney et al. | |
| 2008/0172097 A1 | 7/2008 | Lerch et al. | |
| 2010/0042106 A1* | 2/2010 | Bryant | A61B 17/8869 606/103 |
| 2012/0323241 A1 | 12/2012 | McCellan et al. | |
| 2013/0261625 A1 | 10/2013 | Koch et al. | |
| 2015/0313656 A1 | 4/2015 | Hulliger | |
| 2019/0046253 A1 | 2/2019 | Stecco et al. | |
| 2019/0117265 A1 | 4/2019 | Stecco et al. | |
| 2020/0253654 A1 | 8/2020 | Stecco et al. | |

FOREIGN PATENT DOCUMENTS

| | | |
|---|---|---|
| FR | 2906704 * | 11/2022 |
| WO | 2012174562 A1 | 12/2012 |
| WO | 2019032231 A1 | 2/2019 |

* cited by examiner

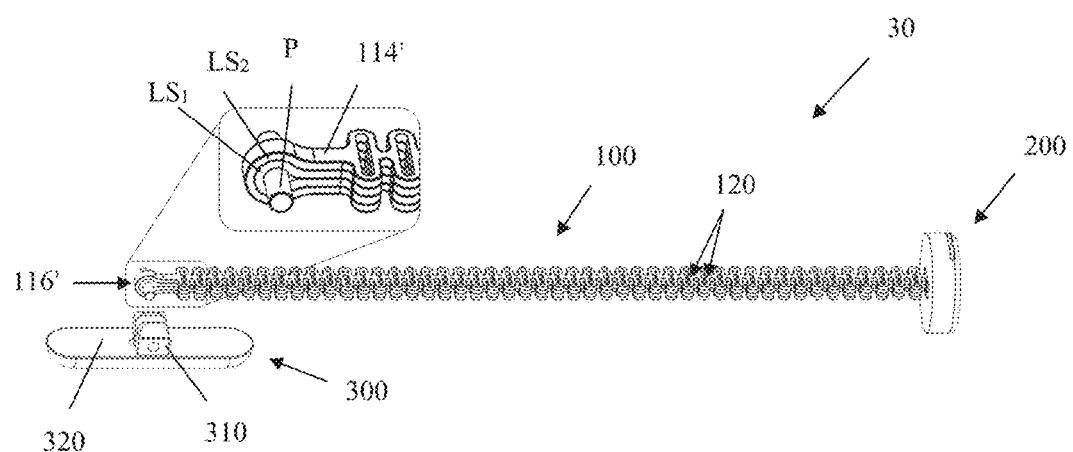
Fig. 1C
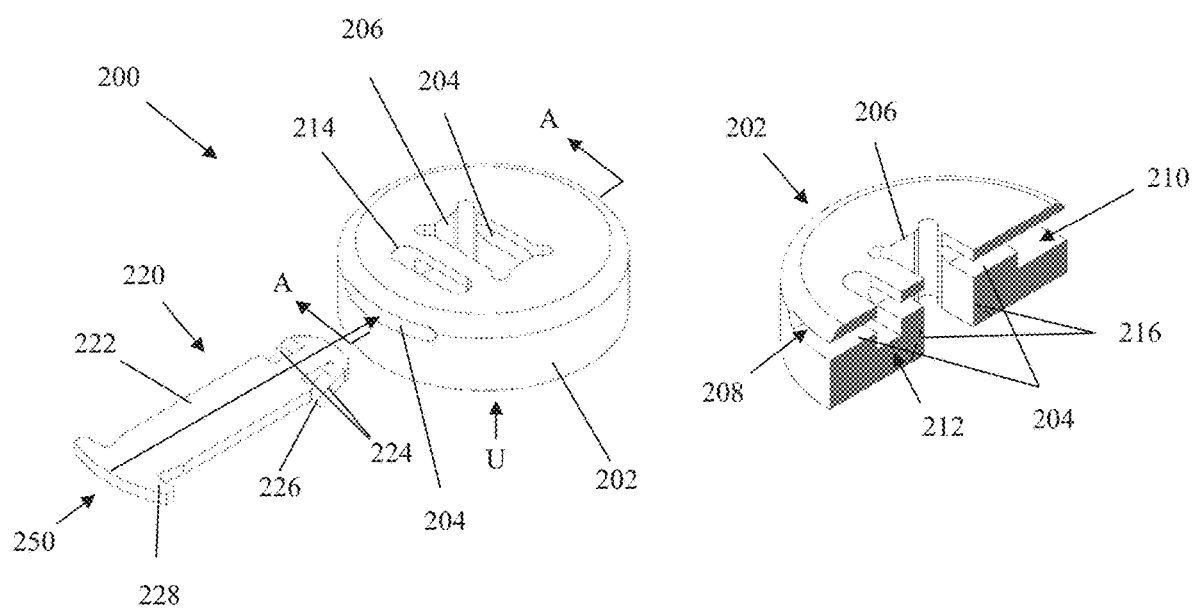
Fig. 2A
Fig. 2B

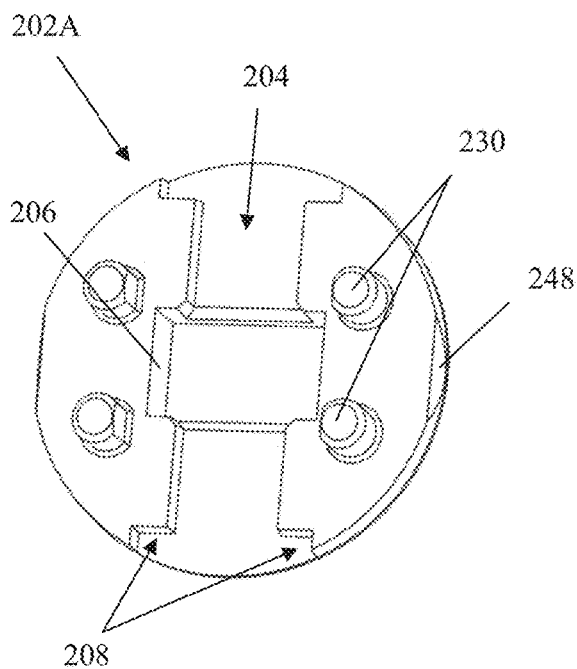
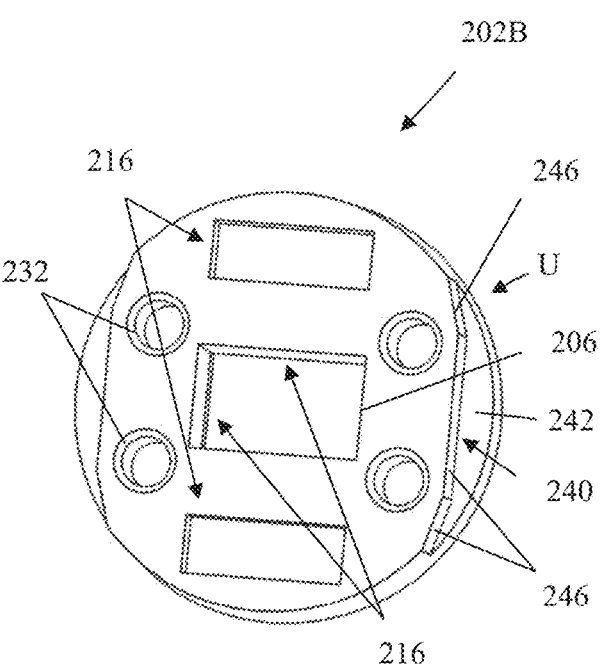
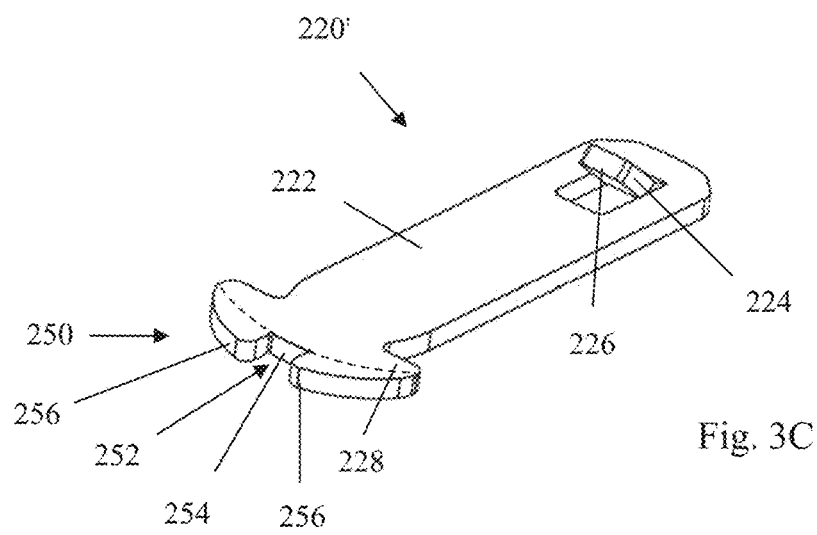

ANCHORS AND TENSIONER AND ANCHOR LOADING SYSTEMS FOR ACTIVE BONE AND JOINT STABILIZATION DEVICES

CROSS-REFERENCE TO RELATED APPLICATIONS

The present application claims the benefit of U.S. Provisional Application No. 62/897,832, filed Sep. 9, 2019 which is incorporated herein by reference in its entirety for all purposes.

BACKGROUND

Various devices have been employed in orthopedic surgery for bone fusion and/or joint stabilization. Bone screws, staples and plates have served as a set of rigid options. Per U.S. Pat. Nos. 4,959,064; 6,656,184; 7,833,256; 7,985,222; 8,048,134; 8,449,574 and 8,491,583 and U.S. Publ. No. 2006/0264954 some screw-type devices have incorporated tensioning springs or members. Button-and-suture type devices have provided a more flexible set of options. U.S. Pat. Nos. 7,235,091; 7,875,057 and 8,348,960 offer examples of such device and suitable applications therefor.

Another class of flexible fixation devices has been described by Panther Orthopedics, Inc. (the assignee hereof) that address many shortcomings of the aforementioned products. The subject anchors and tensioner and anchor loader devices are advantageously used therewith (or with similar implantable devices) as may be appreciated by those with skill in the art in review of the present disclosure.

SUMMARY

U.S. Provisional Patent Application Ser. Nos. 62/837,579 and 62/896,302 included in non-provisional U.S. patent application Ser. No. 16/855,584, each entitled, "STRENGTH AND FATIGUE LIFE IMPROVEMENTS FOR ACTIVE BONE AND JOINT STABILIZATION DEVICES," and each incorporated by reference herein in its entirety, describe embodiments of bone and/or joint stabilization devices that can be tensioned during a medical procedure to remain active in maintaining compression of associated anatomy during use. Related implants are described in U.S. Pat. Nos. 10,194,946 and 10,555,766 also incorporated by reference in each of its entirety, as well as other co-owned patent applications and foreign counterparts.

The instruments described herein are able to controllably tension such devices and possibly others that are able to suitable interface with the same. In various embodiments a so-called tensioning "gun" is provided. In other embodiments, a simpler and more compact implant tensioner and anchor loader interface somewhat like those described in Ser. No. 16/855,584 is provided. In which case, such devices may include various additional optional features such as the manner in which an anchoring head of the implant is held and blocked from rotational movement, how a sliding tooth—alternatively regarded to as a (flattened) cross-pin, cross-member or slat—is stabilized against or blocked from rotation or side-to-side movement and/or back-and-forth or fore-aft movement, or the inclusion of a lock-and-release feature to avoid inadvertent system deployment.

Notably, the features regarding anchor retention and/or tooth stabilization may also be included in said gun embodiment or embodiments. In addition, another anchoring head embodiment is disclosed without the sliding tooth. Rather, it includes a multi-piece body that captures its tooth or slat in a pocket during a sub-assembly procedure.

Devices, instrument or systems in which the devices (or device or instrument components or subcomponents) are included (with or without assembly), methods of use (e.g., with implantation, during treatment of a patient while mending and/or for system removal) and methods of manufacture (including assembly of the various components—as applicable—by a technician prior to sale or during a medical procedure by a surgeon) are all included within the scope of the present disclosure. Such systems may include tensioning and/or loading devices, instruments or tools as described herein. The subject methods, including methods of use and/or manufacture, may be carried out in any order of the events which is logically possible, as well as any recited order of events. Medical methods may include any of a surgical staff's activities associated with device provision, implant introduction, positioning and/or re-positioning, and surgical access, closure and/or removal (e.g., as in an explant procedure).

BRIEF DESCRIPTION OF THE DRAWINGS

The details of the subject matter set forth herein, both as to its structure and operation, may be apparent by study of the accompanying figures, in which like reference numerals may refer to like parts. The components in the figures are not necessarily to scale, emphasis instead being placed upon illustrating the principles of the subject matter. The illustrations are intended to convey concepts, where relative sizes, shapes and other detailed attributes may either be illustrated schematically rather or precisely. To-scale features (e.g., as from engineering drawings and/or photographs) may be relied upon as antecedent basis for claim support.

FIGS. 1A, 1B and 1C are side perspective views (with inset detail images) of implant embodiments that may be used with or incorporated in the subject tensioning systems.

FIGS. 2A and 2B are perspective and side sectional views, respectively, of anchoring head components for the implants shown in FIGS. 1A-1C.

FIGS. 3A, 3B and 3C are perspective views of alternative anchoring head components for such implants.

DETAILED DESCRIPTION

Various example embodiments are shown in the figures and further described below. Reference is made to these examples in a non-limiting sense, as it should be noted that they are provided to illustrate more broadly applicable aspects of the devices, systems and/or methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims that can be made herein.

Example Implant Embodiments

Figure 1A:
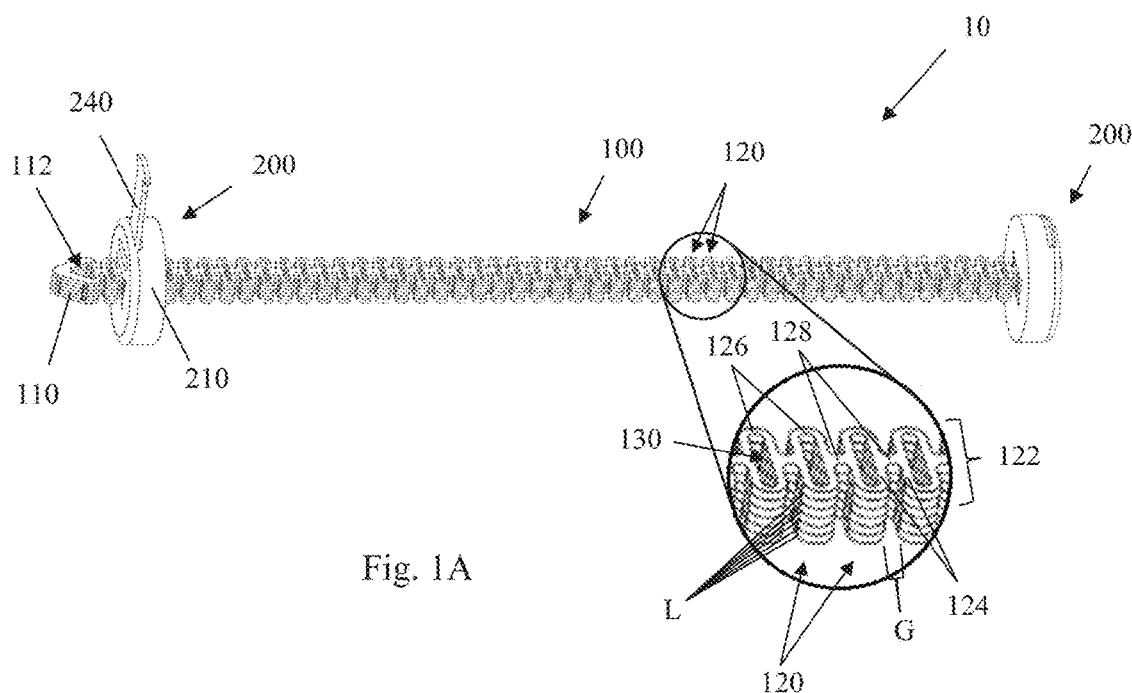

FIG. 1A shows a first implant embodiment 10 including an elongate spring member 100. In this embodiment, two opposite-facing anchors or anchoring heads 200 are used in association with the spring member. Alternatively, the anchoring heads 200 may be referred to as buttons or button-anchors and may be substantially flat or generally disc shaped and have a round, hexagonal or square geometry and may be comprised of a domed or radiused cap or top and/or may have vertical or angled sides (such as by the inclusion of draft angle along a normal, and vertical axis of the component for molding).

Figure 4:
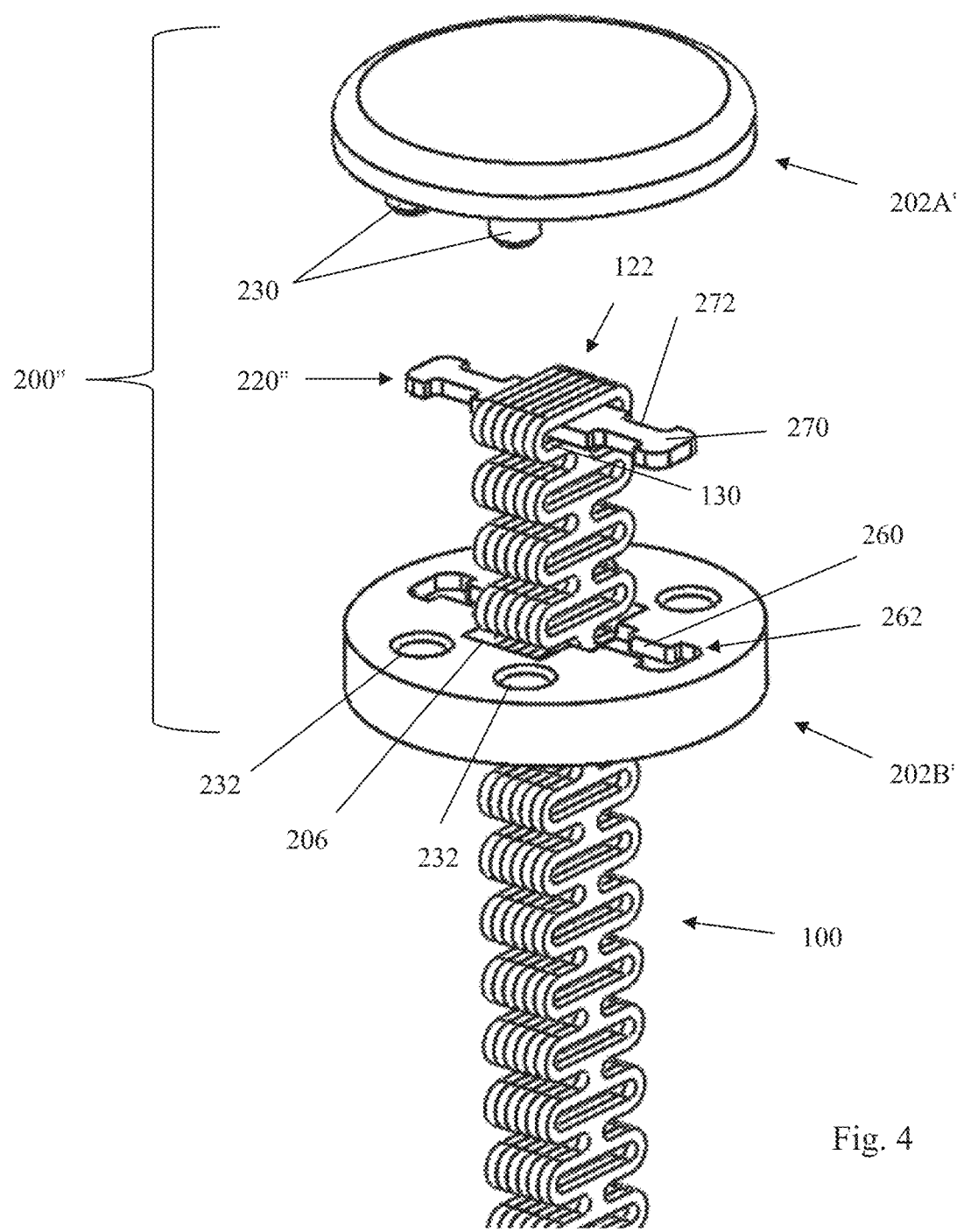
FIG. 4 is an assembly view yet another anchoring head embodiment illustrated together with a portion of a spring member body.

The spring member 100 in this embodiment 10 may include the addition of tab(s) 110, each defining an eyelet 112. A similar tab feature is disclosed in U.S. Publication No. 2019/0046253 and PCT Publication No. WO 2019/032231 for tying on or otherwise securing an associated introducer so-called "Beath" needle with a length of suture or other cordage. As such, only one such tab/eyelet feature 110/112 need be used in the device 100 when one of the anchors (e.g. as anchor head 200 shown at right in FIG. 1 or employing an alternative anchoring head 200" as shown in FIG. 4 as later discussed).

In use, the needle (not shown) is passed through a clearance hole drilled in bone and/or cartilage or other tissue and used to pull the spring member therethrough. The leading end of the implant 10 body self-centers relative to the bore or tunnel through which it is passed given the triangular shape of the associated tab 110 and eyelet 112. Finally, tab 110 is/are trimmed off together with any associated extra length of the elongate spring member 100 that remains upon securing the anchoring head(s) 200 after tensioning. As in the above-referenced patent and patent applications, such trimming may be accomplished with a flush cutter (e.g., a so-called "McIndoe" cutter), a custom tool (such as noted below) or otherwise.

Figure 1B:
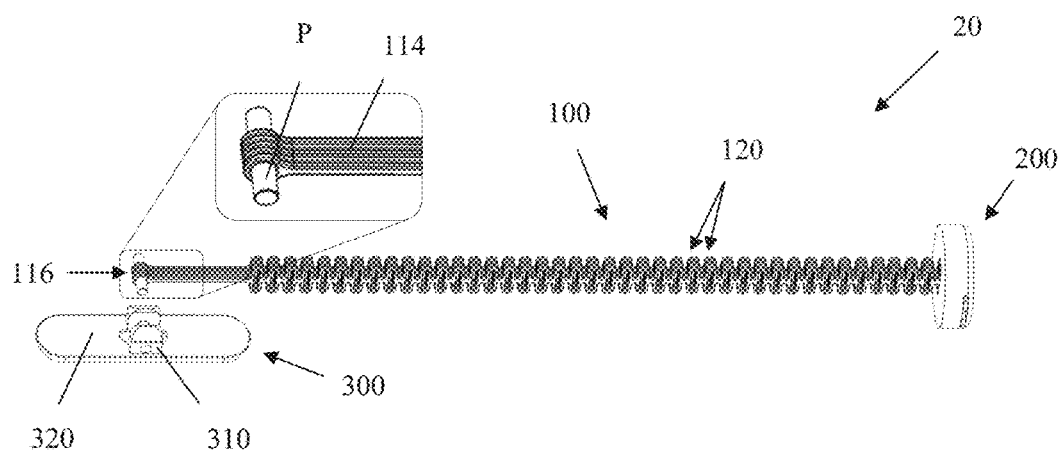

The elongate spring member body 100 may comprise four or more layers (L) as shown in FIGS. 1A-1C and as further described in U.S. patent application Ser. No. 16/855,584. Otherwise, a single-layer or double-layer constructed as described in each of U.S. Pat. Nos. 10,194,946 and 10,555,766 or US Patent Publication US2020/0253654, respectively, may be employed. Three-layer spring members may also be employed, although they may lack certain of the advantages described in connection with the different implant embodiments referenced above.

In all these implant variations, a repeating-cell architecture of the elongate spring member 100 is advantageously employed as detailed in FIG. 1A. Stated otherwise, the elongate spring member 100 of each implant is typically in the form of axially stretchable or spring-type architecture that includes a plurality of connected cells 120 including multiple beams or beam members 122. The beams 122 each include a lateral or cantilever bar component 124 free to deflect for stretching the spring member 100 (or spring member layers) axially. The plurality of beams 122 are arranged in pairs, where a first beam and a second beam of each pair are connected to each other only at the two lateral outer extents 126 such that the first beam opposes the second beam. Each lateral outer extent 126 serving as a connector between paired beams 122 may be a curved continuation of each bar 124 or be otherwise configured. Each pair of beams 122 is connected to an axially adjacent pair by a medial connector or bridge 128. As such, gaps (G) are present at the two lateral outer extents 126 between each pair of beams 122 and the adjacent pair of beams 122 as shown (corresponding to bridge 128 length). The beams 122 or beam pairs serve as leaf spring elements in series that are arranged in cells 120, each with a central window or aperture 130.

The shape of these (integral or integrated) cell elements 120 may present as a race-track configuration as shown. Within the same basic description above, the various beams 122, bars 124 and connectors 128 may be configured in substantially rectangular, oval, circular or other cell 120 configuration (e.g., including more complex aspects such as stress-relief features as shown FIG. 4B of U.S. Pat. Nos. 10,194,946 and 10,555,766 referenced above).

In any case, FIG. 1B illustrates a second implant embodiment 20. It includes one anchoring head 200 (optionally as above) and a pivoting foot anchor 300 at the end of the elongate spring member 100. The anchoring head 200 is shown after application by one of the subject tensioning and/or anchor loading embodiments as further described below. Like the other implant embodiments, the elongate spring member 100 is shown without specific regard to in-situ length; also, it is illustrated after trimming any excess implant length and/or tab (not shown) to the right—as viewed—of the anchoring head 200.

Regardless, implant embodiment 20 includes a straight, axial or longitudinal extension 114 from each layer L in the spring member section 10. Each layer's extension includes a terminal eyelet 116. A single cross pin (P) is received through the eyelets and received in opposing bosses 310 of the foot anchor extending above a base 320 of the anchoring foot. A press fit (in either the eyelet(s) or the bosses) may be employed to hold the components together.

FIG. 1C shows a third device or system embodiment 30. Like the embodiment in FIG. 1B, one anchoring head 200 and a rotatable pivoting foot anchor 300 comprising a base 320 and opposing bosses 310 is used. In device 30, however, the orientation of the spring member cells 110 as compared to the base 320 of the of the pivoting anchoring foot 300 is rotated by 90 degrees. This is accomplished by forming an eyelet 116' for the pin (P) with bent over and headset layer segments $LS_1$ and $LS_2$ as shown. It is also notable that the extension 114' in this embodiment may be appreciable shorter (allowing for inclusion in relatively more cells in the spring member body for a given operative length between anchors 200 and 300) given the orientation of the anchor base 320 relative to the spring member (i.e., for a given clearance hole size or crossing profile).

Further aspects and optional complementary features (e.g., means providing a bias on the anchoring foot 300 towards the transverse position by an integral or a supplemental spiral spring (not shown) to aid transition from the foot's axial delivery configuration to its implanted position) may also be provided in either embodiment 20 and/or 30 as described in US Patent Application US2020/0253654 or otherwise. Overall, other implant configurations suitable for use with the subject tensioning and anchor deployment systems are presented in US2019/0046253.

FIGS. 2A and 2B detail the anchoring head 200 configuration shown in with FIGS. 1A-1C. FIG. 2A illustrates the anchoring head body or base 202 before crossing tooth 220 insertion through cross-channel, track or tunnel 204 and spring member 100 receipt through transverse feed opening 206.

The sliding tooth piece 220, which can alternatively be referred to as a (flattened) cross-pin, slat or cross-member, includes a spanning portion or section 222 and a deflectable latch in the form flexible flap(s) or tang(s) 224 that can move up-and-down relative to the flat underside U of the anchoring head when passing through channel cross-channel, track or tunnel 204 defined in body 202. When overhang sections 228 of the tooth abut stop sections 208 recessed in body 202, ends 226 of each tang will lock when received in a pocket or receptacle 210 formed in the anchoring head body 202. Prior to such deployment or actuation, a releasable detent feature holds tooth position (part way into the anchoring head) by the interaction of tangs 224 with pocket or cavity 212 machined or molded from above (e.g., as illustrated in connection with slot 214) as seen in FIG. 2B. (and which configuration of the anchoring head with its captured-but-undeployed tooth is detailed in FIG. 6). FIG. 2B also illustrates optional chamfer or lead-in features 216 (illustrated in dashed line) for spring member receipt that may be machined or molded into the body or base and may take the form of angled surfaces as indicated, or be curved or cup-shaped.

Figure 10:
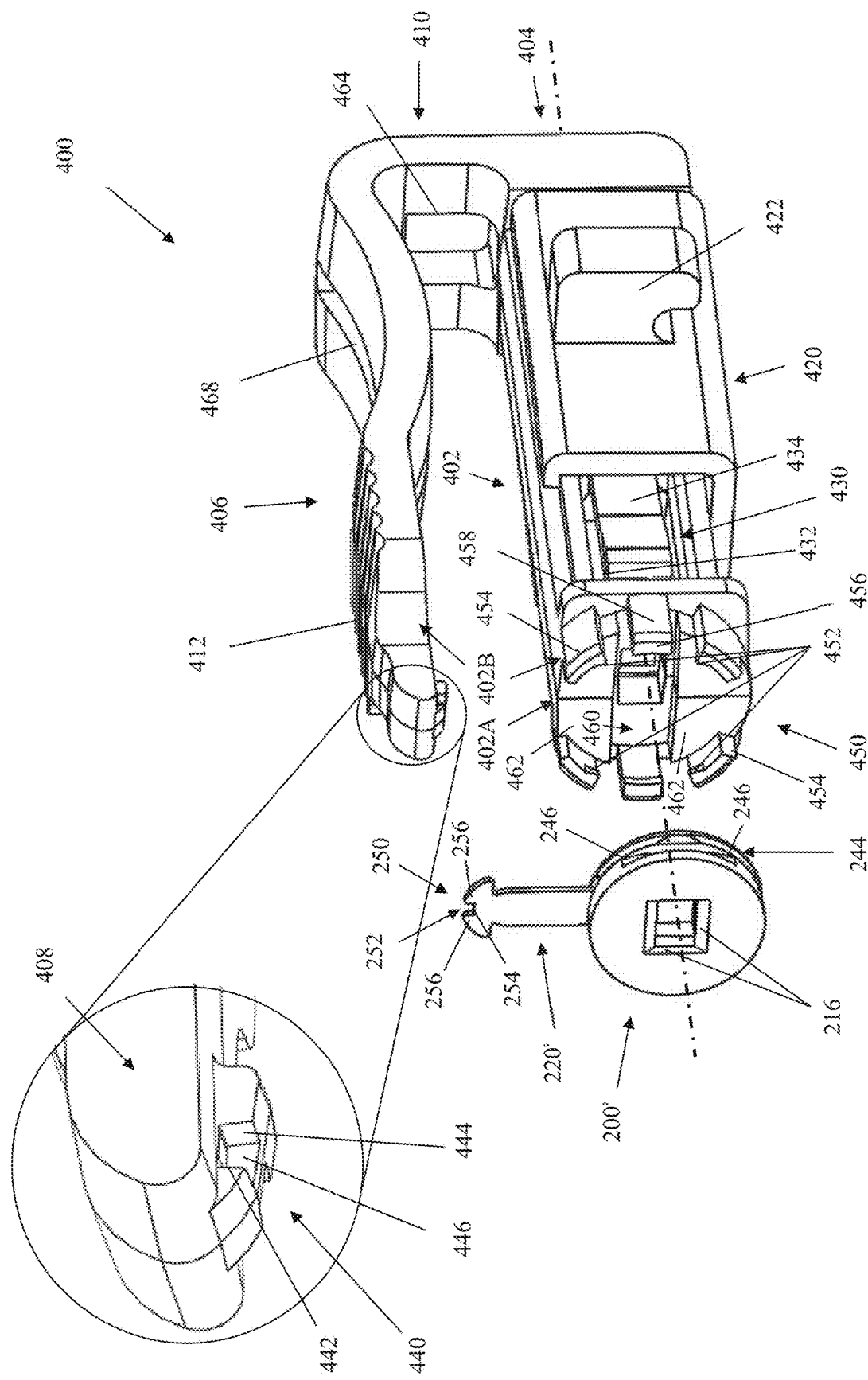
FIG. 10 is a perspective view of another tensioner and anchor loading instrument embodiment.

In any case, FIG. 3A is a perspective view of an upper or outer body piece or portion 202A of another anchoring head example embodiment. FIG. 3B is a perspective view of a lower or inner body portion 202B of the same. When connected (and loaded their associated sliding tooth, optionally as pictured in FIG. 3C), the assembly forms a second anchoring head embodiment 200' as shown in FIG. 10.

Such connection or attachment may be made by an interference fit between pegs, posts or pins 230 within sockets or pockets 232 (or through-holes) in part 31B. Or the pins may be carried by body 202B and the sockets or through holes made in part 202A. Either way, the pins may be round, hexagonal or D-shaped as shown to include flats for air to pass out of the sockets (shown) during a press-fitting procedure.

Body piece or portion 202A includes a spring member feed opening or aperture 206 and a slot 204 that defines a closed channel when body portions 202A and 202B the parts held or secured together. Stop sections 208 may be provided, as above, for locking the proximal end(s) or overhand portions 228 of tooth 220 in place once fully deployed in the anchoring head.

Body piece or portion 202B also includes a transverse feed opening 206 that aligns with that of its complementary piece. In addition, body piece 202B includes one or more pockets or troughs 216 (serving the same purpose as features 210 and 212 in the previous embodiment) to receive the deflectable latch portion(s) 224 of the tooth to be used. Symmetrical shape and/or placement of pockets 216 can be of assistance for assembly (making the part non-directional with respect to the slot 204).

In another optional aspect, either one (or both) of pieces 202A and 202B may include a side-cut or inset regions 240, each to produce a ledge 242 to define opposing side slots 244 (shown in FIG. 10) for holding the anchoring head apart from its underside (U) when the pieces are assembled. Various flat sections or "flats" 246 may be defined for coordinated use. A ramp section 248 may also be included to ease anchor loader removal. In addition, spring member lead-in section or sections 216 may be provided as described above (also shown in FIG. 10).

FIG. 3C is a perspective view of an another sliding tooth embodiment 220' that may be used in connection with the anchoring head pieces (once assembled). It may also be used in other anchoring head embodiments, including that illustrated in FIGS. 2A and 2B referenced above.

Cross-pin or tooth 220' includes only one, central locking tang 224. For assembly, it is (essentially) flipped over and received in complementary socket or pocket features 210 and 212 or 216 depending on the embodiment selected. Note, however, such pocket or socket features may be reversed (i.e., located in the cap vs. the base). In which case, either of the teeth selected will be used with their tangs facing upward (i.e., toward the cap).

In any case, a crown 250 of the tooth 200' is shown including indexing features for use as further described below. An inset region 252 include a base or bottom surface 254 set to align with the edge of the anchor body when the tooth is fully deployed or received therein. Bosses, nubs or shoulders 256 are provided on either side of the inset region. These may be radiused as shown. These crown 250 features interface with those shown and described in FIG. 10 to constrain rotational (side-to-side) and front-to-back or fore-and-aft motion (such constraint of motion is optionally referred to as "clocking" herein) of the tooth 220' when partially set within the anchor body 200, effectively eliminating undesirable motion play as a result of tolerance considerations.

This configuration has the advantage of relatively small or unobtrusive features extending past the circumference or border of the anchoring head 200 (especially as compared to the effect of a central nub captured by a pocket within the anchor loader pusher arm) as indicated by the included phantom line in FIG. 3C.

FIG. 4 is an assembly view of another anchoring head embodiment 200". Here, top and bottom body pieces 202A' and 202B' capture a cross-pin or tooth 220' in a trough or pocket 260 after the tooth is passed through the end-most aperture 130 of a spring member 100 received through the feed opening 206 in the lower body portion. The cap is optional and may be press-fit with pins 230 into sockets 232 or the connection features may be reversed—among other options.

As above, the anchoring head 200" may be regarded as disc-shaped or in the form of a substantially flat button. Still, the cap portion 202A' may have a slight domed or radiused profile if desired. Depending on the thickness of the cap piece 202A', accommodation for the proximal-most beam(s) 122 of the implant body may be provided by a through-hole (like clearance hole 206 shown in the cap of FIG. 3A) or a hidden pocket (as is the case in FIG. 4).

Another option is to include knob-like features 270 adjacent necked-down regions 272 at each end of the tooth giving it a "dog-bone" shape. These knobs (be they round, triangular or otherwise shaped) are sized and shaped to engage and conform to the inner circumference of the complementary capture features 262 at each end of the trough 260 disposed in the bottom body piece 202B'. Such configuration may offer further strength or stability to the system by putting the tooth in tension as well as shear when pulling on the captured spring member.

As in the other anchoring head embodiments, the crossing tooth 220" is typically constructed in NiTi. However, in this instance, Stainless Steel may be used as a deflectable tang (like element 224 in either of teeth 220 or 220') that may be reliant on the superelasticity of NiTi alloy is not included.

Also like the other anchoring head embodiments, the body components may be injection molded or machined polymer (such as polyether ether ketone, a.k.a. PEEK). Such material may be doped with barium sulfate for radiopacity. Alternatively, such components may be made from metal (e.g., Stainless steel) or include metal marker(s) for radiopacity.

Tensioner and Anchor Loader Embodiments

Figure 5A:
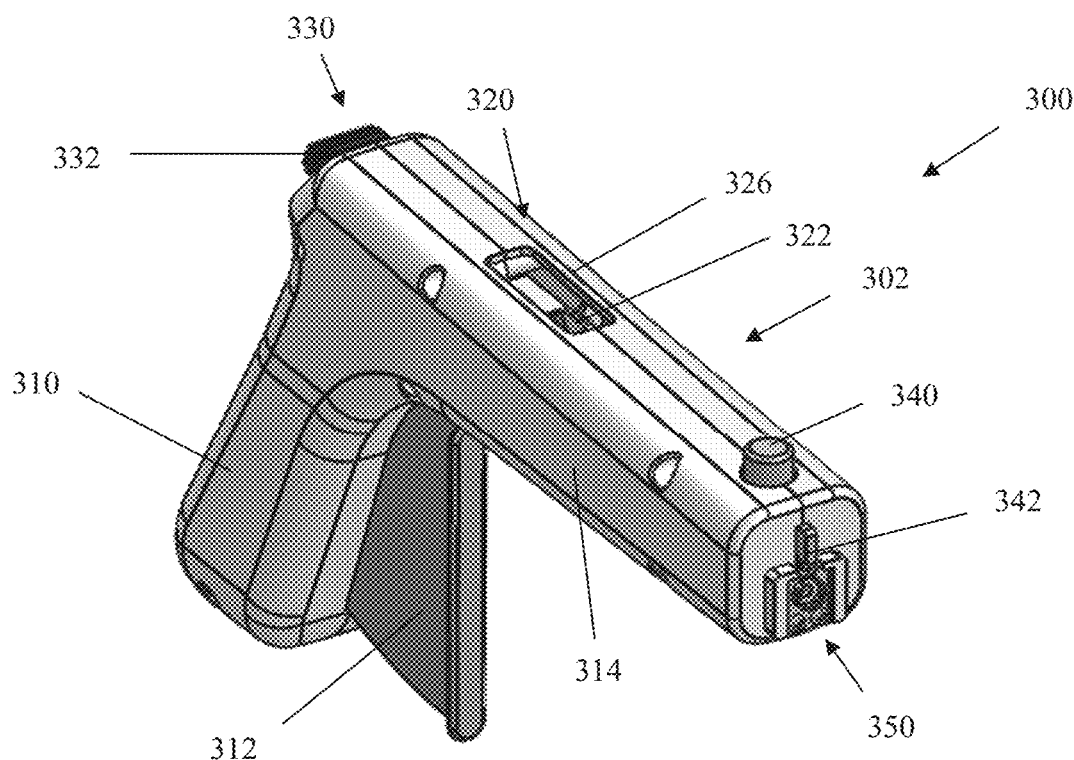
FIGS. 5A and 5B are front and rear perspective views, respectively, of a tensioner and anchor loading instrument embodiment.
Figure 5B:
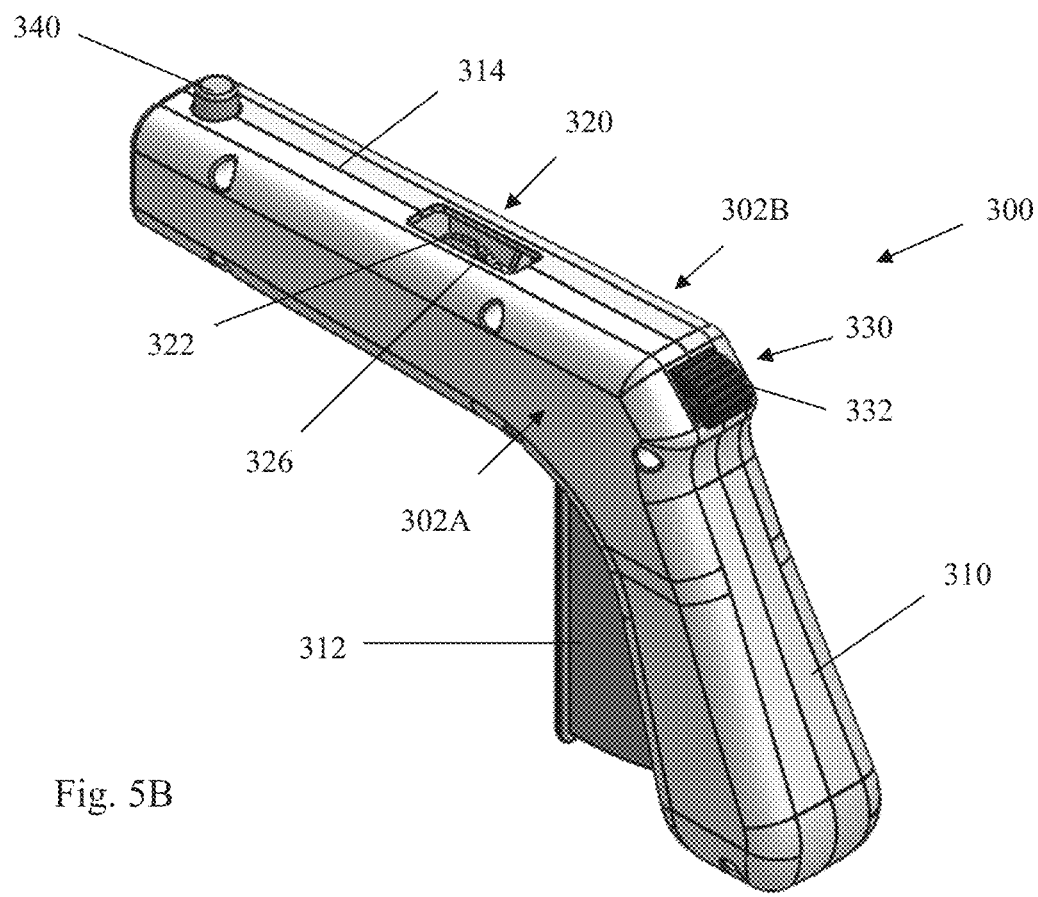

FIGS. 5A and 5B are front and rear perspective views, respectively, of a tensioner or tensioning and anchor loader or loading instrument 300 (or simply a medical instrument) embodiment. These exterior views show a hand-actuated medical instrument interface comprising a body 302 formed in two half pieces 302A and 302B and including a hand grip or handle section 310, an actuator that may be positioned as a trigger section 312 and a transverse housing formed as a barrel section 314.

A visual tension indicator 320 is disposed in a lateral surface of the transverse housing. And performs the function of displaying tension exerted on the implant 10 b the loading instrument 300. Examples include a scaled gauge 322 and a tension indicator needle 324 (seen in subsequent figures) each visible through a port or window 326 that may simply be an open aperture or include a clear plastic cover or pane (not shown) within the aperture. The tension indicator may be quantitatively calibrated based on the axial spring characteristics of the elongated spring member 100 and display gradations of force or distance indicating tension generated in the spring tensioner 300 (and in equal measure in the implant—not shown in this view) may be between 0 and about 10 lbf, or to a limit of 8 lbf, 6 lbf, 4 lbf or between about 2 and 3 lbf, such as 2.5 lbf. Regardless, the architecture shown is flexible and the gradations or scaling can be varied in connection with the selection of the spring(s) with different spring constant(s), such that selection of an individual embodiment of the elongated spring member 100 corresponds to a calibrated tension display of the visual tension indicator 320 specific for the physical characteristics of the elongated spring member 100.

To provide the hand-actuated function, one embodiment of the invention utilizes a thumb grip or hammer 330 provided as an interface to a tension release pawl (described below). A push button 340 to actuate a pusher extension 342 for the sliding tooth or cross-pin 220 is provided at the distal end 344 of the elongated housing formed as barrel 314 as shown in FIG. 5B and detailed in FIG. 6. The anchor 200 (also shown in FIG. 6 but not shown in FIG. 5A) is held in interface cradle 350.

The implant body and its anchoring head may be as described in the above-referenced patent applications that are commonly assigned to Panther Orthopedics. For instance, the implant may be a single-layer implant and the anchoring head include one or more one-way or ratcheting teeth as in FIGS. 4A-4C (specifically incorporated by reference herein, together with associated text) of US Patent Application Publication US2019/0046253. In another example, a two-layer implant is used with anchors as described in FIG. 6 (specifically incorporated by reference herein, together with associated text) of US Patent Application Publication US2020/0253654. In either case, all of the mechanism(s) described in association with the subject medical instrument 300 may be used in tensioning the subject implant except for the push button 340 for tooth deployment. Namely, each cell of the elongate member selected that is pulled through the anchoring head may be automatically locked in the anchoring head held by medical instrument 300. Otherwise, the function is as further described below.

Returning to FIG. 6, a multi-layer implant body (its spring member 100) is received within the anchor. In practice, the elongate spring member 100 would be located within a bone tunnel and the anchoring head 200 (or gripping "nails" 352 at the end of flexible, releasable "fingers" 354) abutting bone or a plate thereon with the distal anchor. Further options and description for these features may be appreciated in reference to US Patent Publication US2020/0253654 and/or U.S. application Ser. No. 16/855,584, each incorporated by reference for such purposes (or any others).

Once spring member 100 is inserted through the clearance hole or aperture 206 of the anchoring head and through socket 350 into contact with internal grippers 372 (described below) one or more strokes or compression cycles of the trigger 312 causes a self-energizing grip on the implant. The implant is then tensioned employing one or more additional strokes or compression cycles of the handle.

The component parts of medical instrument 200 may be configured such that each compression cycle tensions the spring member 100 along the longitudinal axis thereof by one cell 120, whereby the cells between the proximal anchor and the distal anchor are stretched and/or the distance between the anchors is (at least somewhat) decreased thereby reducing associated anatomy therebetween. The internal mechanism of the tensioner 300 maintains force exerted along the longitudinal axis of implant/spring member tension when button 340 is depressed. Continuing to refer to FIG. 6, such action moves extension 342 to push the crossing tooth through the anchoring head, across an opening 130 in the spring member. Clearance (C) between the crown 250 of the sliding tooth 220 and the pusher surface 344 may be provided. Otherwise, engagement between tooth indexing features like those shown in FIG. 3C with complementary pusher features as illustrated in FIG. 10 may be employed.

In any case, the medical instrument 300 is configured to index tensioning of the elongate spring member 100 so that it is properly aligned after each compression stroke for tooth or cross-pin deployment and appropriately configured for the next actuation of the hand-held tensioner. Stated otherwise, the relative size and spacing of the grasper and gearing components as further described below are such that the cross pin is aligned with a window 130 in any given cell 120 after the prior trigger 312 actuation.

After cross-pin deployment, tension on the portion of the implant body being held by gripper(s) 372 is released by withdrawing the hammer 330 pulling its grip 332 backward or downward (toward the user) to disengage a pawl section from associated gears 368. As shown in the assembly view of FIG. 7 and the cross-section view of FIG. 9B, until withdrawn, a leaf spring 334 biases the hammer assembly 330 forward around its pivot pin (P).

Note, however, integrated bosses (formed either in the shell or captured mechanism pieces) may be substituted for the various bearing housings 304 and pivot pins (P) pictured. Likewise, included screw sockets 306 and interfacing screws(s) may be eliminated in favor or snap fit, press fit and/or other features. Alternatively, welding (e.g., ultrasonic welding, as many of the component pieces of the medical instrument are advantageously made of plastic, e.g., nylon) or other means may be employed as well.

Figure 6:
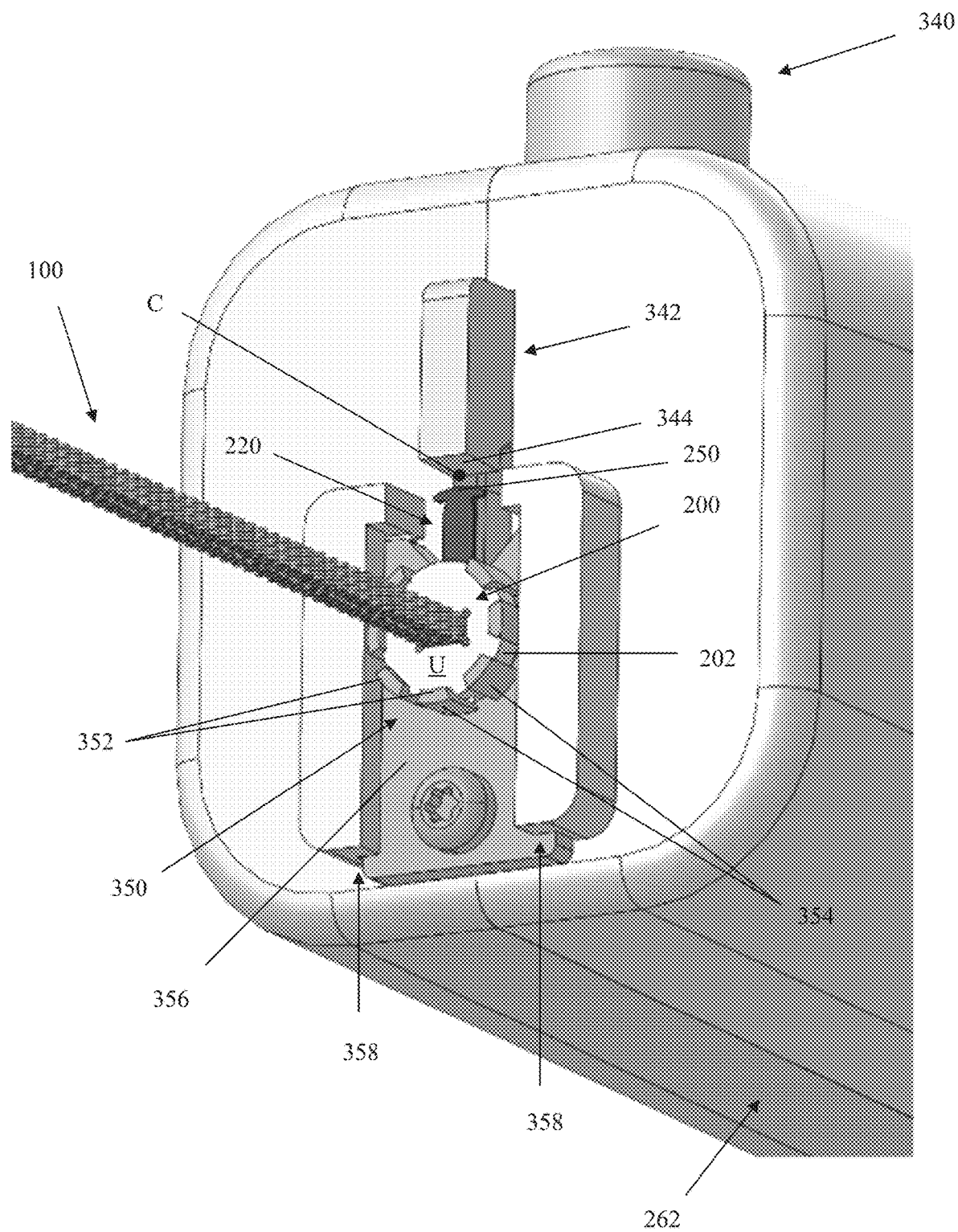
FIG. 6 is a front perspective, detail views of the medical instrument receiving an implant body and anchoring head.

Referring to FIGS. 5A, 5B and 6, once the crossing tooth 220 is deployed, the self-energizing hold of grippers 372 on the implant 100 is released by actuating the hammer 330 (or another suitable interface means). Then, the tensioner 300 may be pulled free of the anchor with the fingers 354 flexing to release the captured underside (U) surface of the anchor from the finger "nails" 352. To assist in such action, each of the tips or nails may include an undercut ramp section (not shown).

After the tensioner 300 is removed the spring member 100 may be trimmed flush with the anchoring head 200 using side cutters (such as McIndoe cutters) or other means. Otherwise, it is contemplated that cutting features may be integrated in the tensioner 300 and the cutting performed prior to anchor removal from the socket 350.

Figure 7:
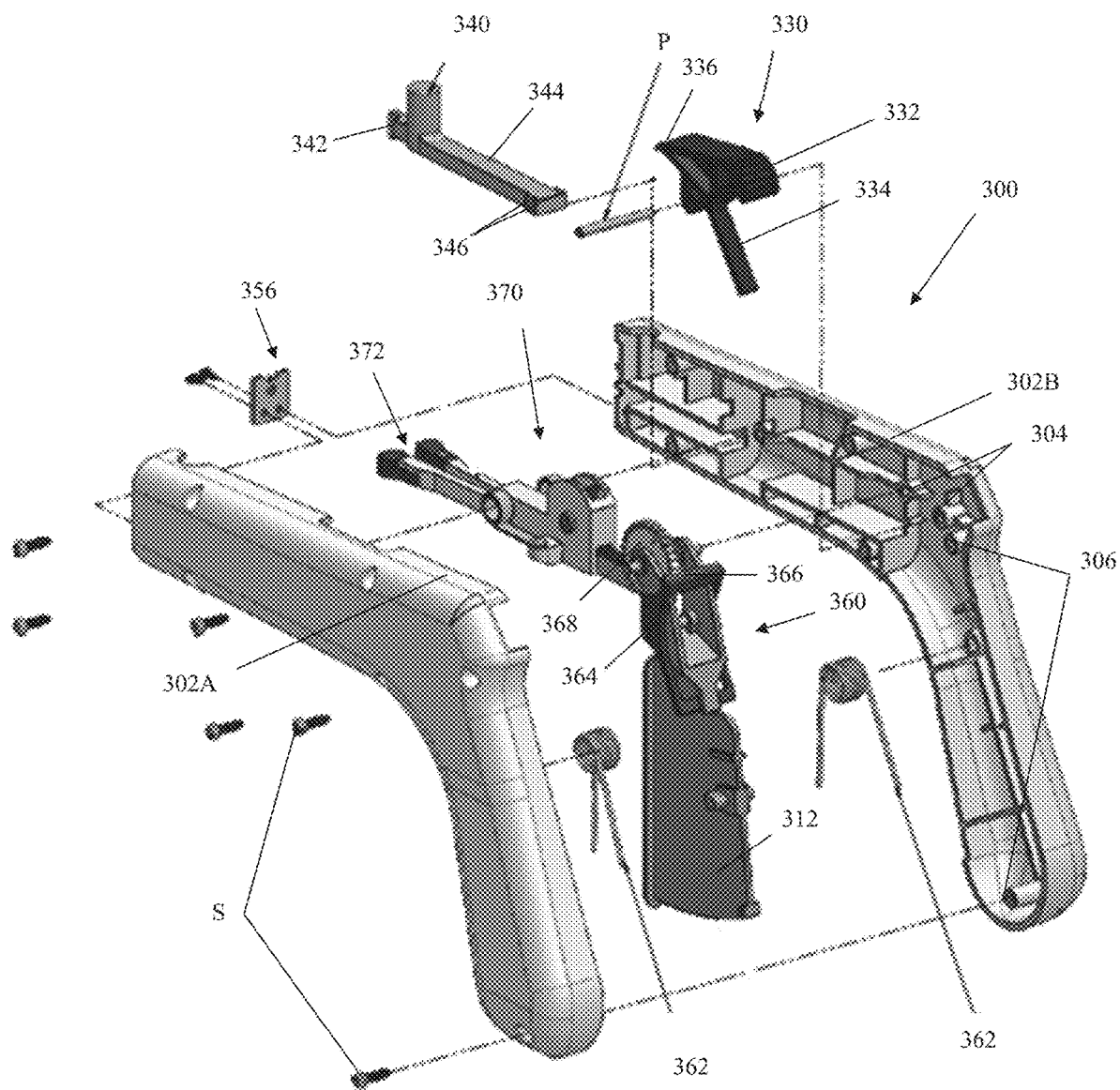
FIG. 7 is a partial assembly view of the tensioner and anchor loading instrument illustrated in FIGS. 5A, 5B and 6.

Referring to FIG. 6, the cradle or socket 350 is shown included as part of an insert 356 received within guides 358 and secured by a bolt or screw (two such screws in the variation shown in FIGS. 5 and 7). The guides 358 are separated and oppositely opposed to receive the socket 350 and insert 356 includes a "U" or "V" shaped inset for clearance to allow the pusher extension 342 to depress and advance the sliding tooth 220 downward until it contacts the surface of the anchor body 202 and sets the top surface of crown 250 of the crossing tooth 220 flush with the anchor body 202.

Returning to FIG. 7, the assembly view reveals further component part details. The pusher button 340 extends upward from a flexible cantilever beam 344 with anchoring features 346 at its proximal end (to be received by the medical instrument body shell pieces 302A and 302B as indicated by assembly lines—although the button beam and pusher could instead by integrally molded with or in one of or both the shell pieces). Other assembly lines illustrate the placement of the remaining parts within the handle shell. Placement of a trigger handle 312, driving pawl and ratchet sub-assembly 360 is so-illustrated as is claw, indicator and rack sub-assembly 370.

The trigger handle 312, driving pawl 366 and ratchet sub-assembly 360 may be constructed as shown. Namely, it may include the handle section 312 to be biased forward with one or more torsion spring 362, an interlocked "stirrup" 364, tipped with a pawl 366 and ratchet gear 368 with both the pawl and ratchet gear rotatable and held on one pin (an axel) and the overall assembly on another (note pin callouts in FIG. 9B). The trigger section 312 and pawl 366 may alternative be integrally produced without loss of functionality, and rotatable around Pin "P" axle as in FIG. 9B with (possibly) increased manufacturing complexity.

Figure 8:
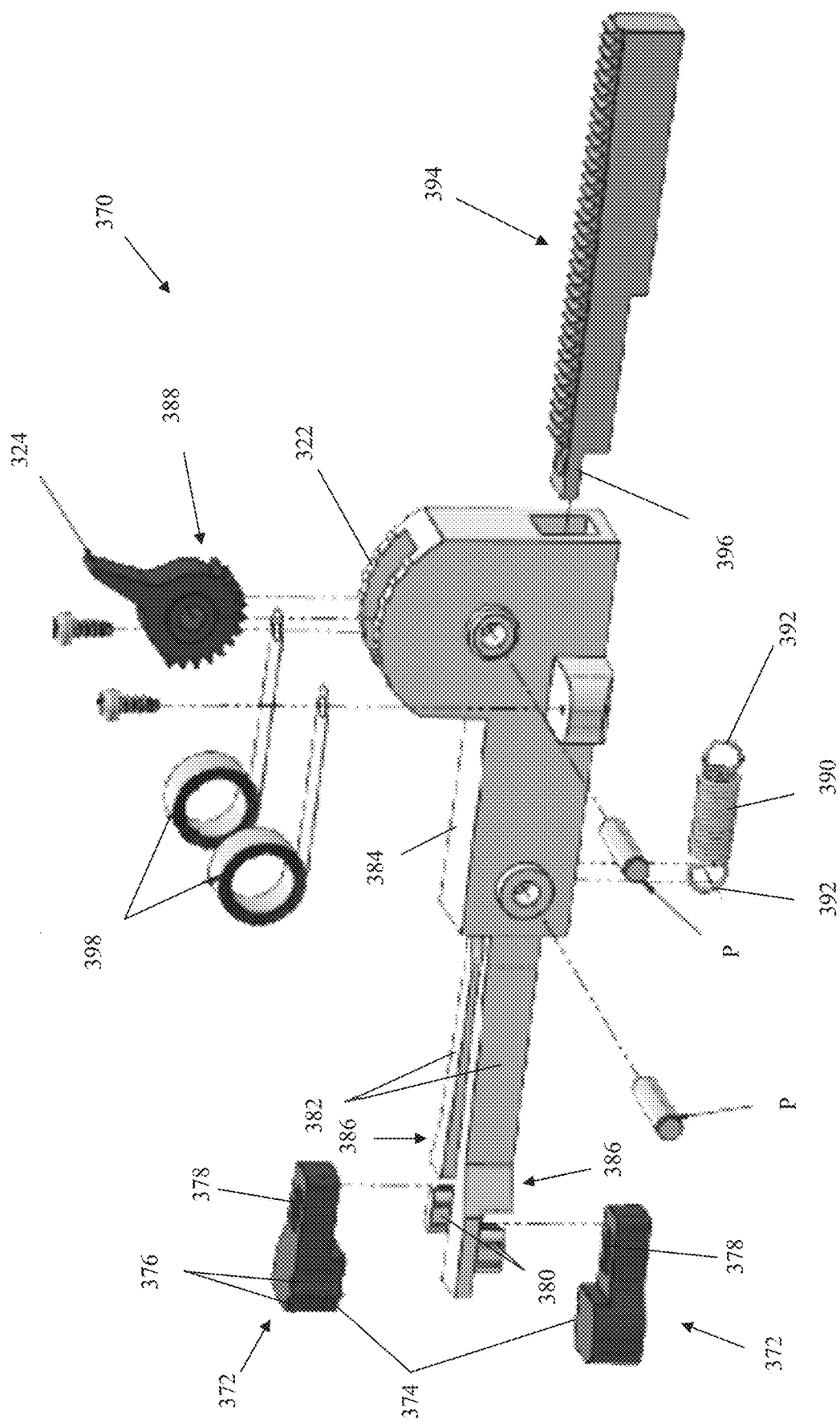
FIG. 8 is an assembly view of the sub-assembly shown in FIG. 7.

The claw, indicator and rack sub-assembly 370 is more complex by its nature and is further illustrated in the assembly view of FIG. 8. Beginning with a gripper or grasper section 372, it advantageously includes hard polymer (e.g., PEEK) or metal (e.g. Stainless Steel) set of graspers 372 including claws 374 adjacent hollows or inset portion(s) 376. The graspers 372 may securely hold complementary portions of and implant body even under high tension. More particularly, the claws 374 fit within the gaps (G) between adjacent spring member cells 120 to form a secure connection when compressed.

As shown, the graspers 372 may be independent pieces including sockets 368 configured to receive posts 380 associated with flexible arms 382. This approach permits construction from different material. An opposite facing (up-and-down) arrangement of the grips or graspers 372 (hands) relative to the arms 382 may be employed as shown.

Otherwise, the graspers 372 may each sit atop flattened hand or palm sections (not shown) or be (or formed) between opposing surfaces integrated with the arms 382. Either such approach may help constrain the position of the spring member 100 when loading it into the instrument for gripper capture. Another approach may be to receive the spring member 100 between fins or baffle walls 316 formed in the outer shell piece(s) with the grippers 372 and arms 382 operating between such features as shown.

Arms 382 extend from or are otherwise operatively connected to a base or body portion 384 of subassembly 370. The arms 382 are flexible to be biased outward upon final assembly. Upon being pulled proximally, ramp sections 386 contacts portions of the housing shell (302A and 302B) driving the graspers inward to grip the implant body. Other configuration options to push at least one gripper inwardly to hold the spring member 100 when the grippers 372 are pulled proximally are possible as well. In any case, an interference type lock is generated that will only be released upon release of overall system tension.

The body portion 384 of sub-assembly 370 is further configured to receive each of the indicator gear 388 (with incorporated pointer or needle 324) to rotate about an axel pin (P) as well as a spring pin (P) to secure an extension spring 390 through one looped end 392. The other looped end 392 of the spring is engaged with rack gear 394 though another loop or hook 396 with the body also receiving the rack gear 394 (sliding or translationally).

Optional constant force springs 398 may be fixed with screws as indicated in FIG. 8 with their coils received within pockets of the shell(s) as indicated in FIG. 7, around pins (not shown) or otherwise. If included in the device, spring(s) 398 assist to return assembly 370 to its forward (distal) position following multiple cycles of the handle after hammer 332 release. This may be a desirable feature to allow for releasing a given spring member and repeating tensioning (for one reason or another) or in the case that the medical instrument is not treated as a disposable or one-use item.

In the embodiment pictured, spring(s) 398 do not set the minimum tension registered by the included gauge as the extension spring (coil spring) 390 is selected or tuned to balance with the constant force spring(s) 398 and start at a net zero force on the spring member 100 upon engagement. Extension (coil) spring 390 can alternatively be tuned through pre-loading to set the minimum tension registered. The constant force spring(s) 398 only significantly affect the force at the pull handle or trigger 312 and operate essentially independently of the extension spring (and force measurement capacity of the device) with exception of the aforementioned calibration.

Figure 9:
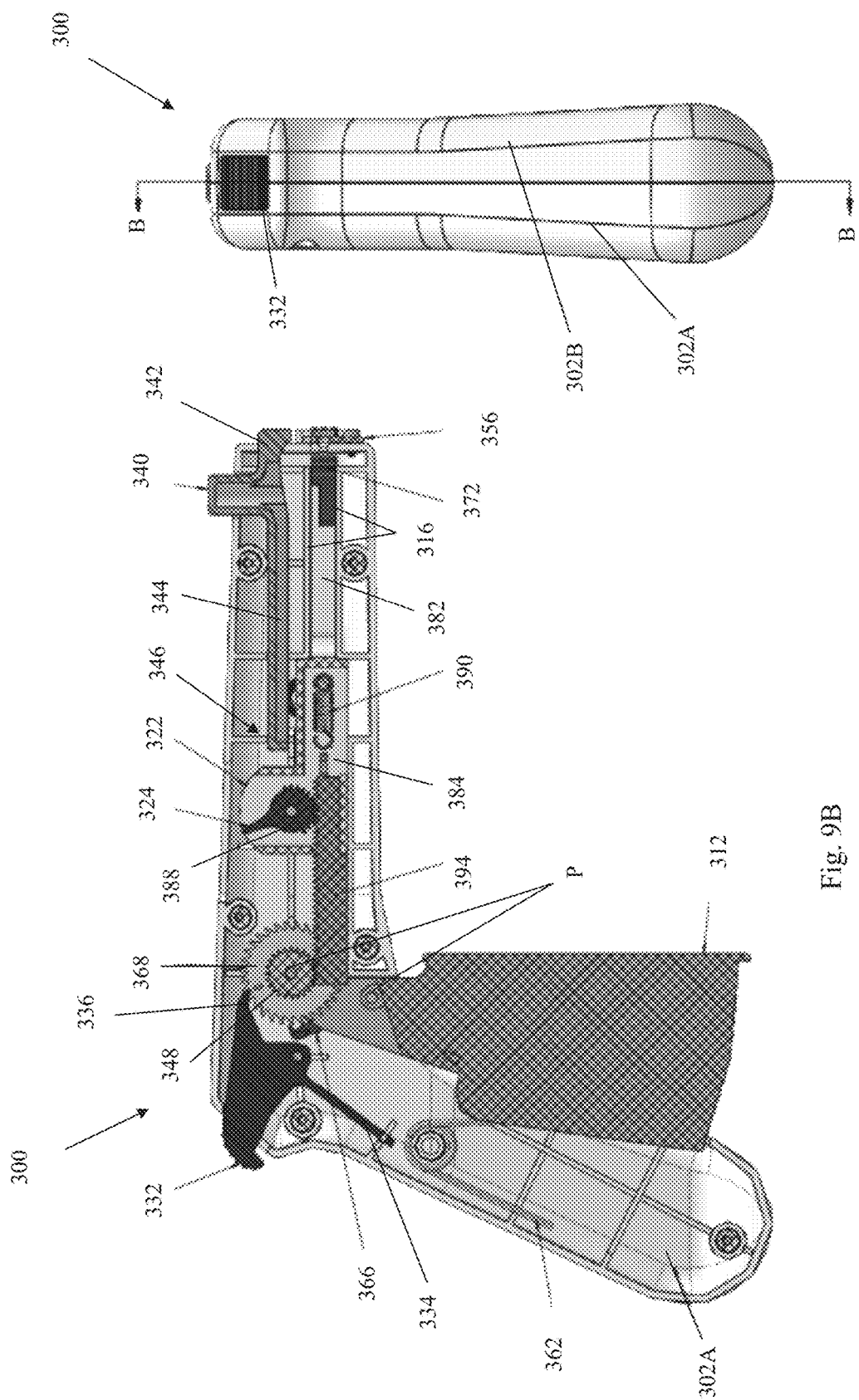
FIG. 9A is a rear end view of the medical instrument variously illustrated in the immediately preceding figures.
FIG. 9B is a side cross-section view taken along line A-A in FIG. 9A.

Still further details of placement the subject components and their interaction may be appreciated in connection with the side-cross section view of FIG. 9B taken along line B-B shown in FIG. 9A. In this cross-section view, the manner in which the trigger handle 312 is backed-up and biased by tension spring(s) 362 is evident, as is the driving pawl 366 associated with the handle.

Upon squeezing the trigger 312, the driving pawl 366 advances an interfacing tooth of ratchet gear 368. The pawl segment 366 of the hammer piece 330 releasably holds driving/ratchet gear 368 position. Teeth of a pinion gear 348 interface with a linear rack 394 with teeth.

With the hammer 330 forward, the pinion gear 348 (sharing an axis of rotation and connected to the ratchet gear, whether formed integrally assembled as parts) turns in unison with the ratchet gear 368, meshing with the rack 394 and pulling it backward which, in turn, withdraws the connected (via spring) housing 384 along with arms 382 and graspers 372 holding a sprig member body 100, thereby tensioning the same.

Accordingly, when holding an implant in the teeth or claws 374 of the subassembly jaws 370 (that is stabilized or anchored outside the tensioning instrument) the tension generated in spring member 100 is indicated by needle 324 in reference to indicator or gauge 322. Notably, the gauge may indicate the actual tensile force or tension applied to the spring member as referenced above. Alternatively, it may present as a color-coded indicator with a so-called "green" zone indicating ideal tension.

In use, the surgeon feeds a proximal end of the elongate spring member 100 into the distal end of the medical instrument 300 with an anchoring head 200 that together form the implanted body held by the medical instrument 300. The instrument 300 is hand actuated so that with each cycle of the trigger mechanism 312 an axial force is exerted along the length of the elongate spring member 100. The configuration of the plurality of cells 120, including the aperture 130, is tensioned by engagement of the implant body with one or more grippers 372 that are operably connected to the tensioning trigger. The trigger mechanism is actuated until the desired tension reading is visually displayed by the tension indicator 320 housed in the body of the medical instrument 300.

The sliding tooth 220 within the anchor head 200 is passed through an aperture 130 in the elongate spring member 100 to secure the tension applied by operation of the trigger mechanism 312. The sliding tooth is actuated by a push-button 340 along a top surface of the medical instrument 300. Tension along the axial length of the elongate spring member 100 may be released by actuating the release pawl to disengage the grippers 372 from the elongate spring member 100 and then tension re-applied, optionally to a different level.

The distal end of the elongate spring member 100 is fixed in place by a rigid structure transverse to the axial length of the elongate spring member, such as the pivoting anchor foot 304 or a second anchor head 200. The pivoting anchor foot can rotate around the opposing bosses 310 to position the length of the base 322 a transverse direction relative to the elongate spring member. Once the desired tension is reached and the proximal anchor locked by sliding the tooth through pushbutton 340, (or by ratcheting tooth actuation within the anchoring head 200 when another proximal anchoring head 200 is used, the implant body is separated from the instrument 300 and any excess length at the proximal end of the elongate spring member 100 may be trimmed, for example segment of the elongate spring member 100 proximal to the most proximal anchoring head 200 a from the implant body and trimming a length of the elongate spring member 100 proximal to the proximal anchoring head.

Figure 11A:
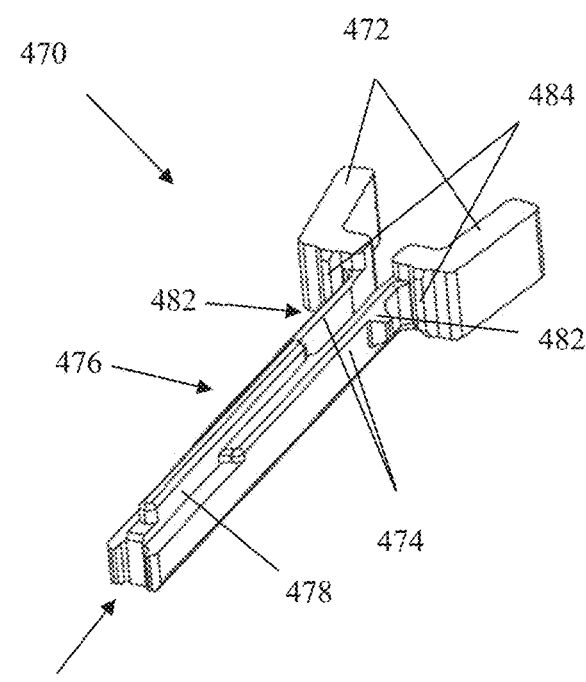
FIGS. 11A, 11B and 11C are perspective views of safety release features that may be incorporated in the medical instrument shown in FIG. 10.
Figure 11B:
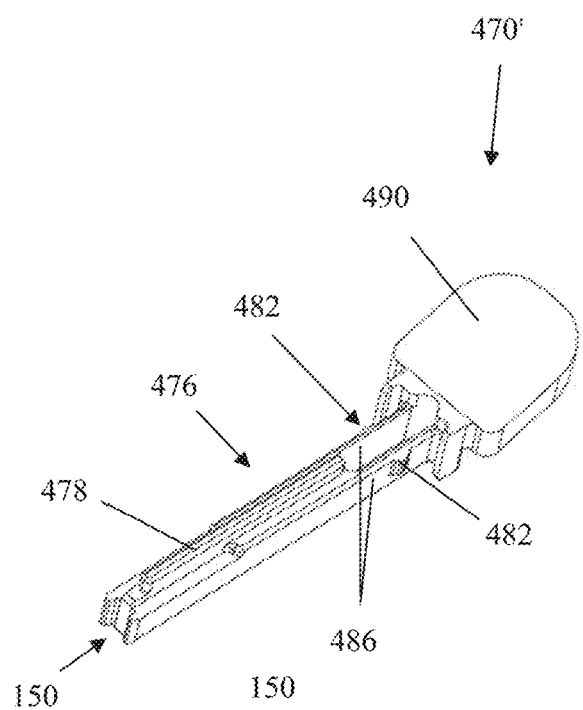
Figure 11C:
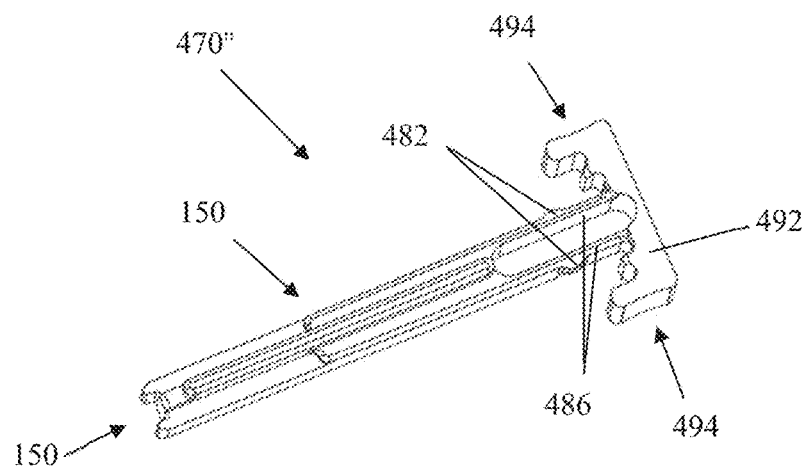

A simpler tensioner and anchor loader embodiment 400 is shown in FIG. 10. While it lacks tension-indicator features as described above, a spring member can still be pulled by a physician (manually or applying forceps to grasp the spring member proximal to the instrument body) to desired tension that is maintained or locked in by pushing slider 420 forward locking detents 430 between cells 120 of the spring member body before anchor deployment. A related embodiment is shown and described in FIGS. 11A-11C of U.S. patent application Ser. No. 16/855,584 incorporated herein by reference. Various novel refinements of the medical instrument 400 are presented herein.

However, more general features are first described. Namely, a plunger-style tool or implement 400 has a body 402 that includes a tunnel or through hole 404 to allow passage of a spring member body 100. It also includes a socket section 450 to receive and releasably hold an anchoring head 200'.

The main body portion 402 of the instrument may be box-shaped or otherwise configured (e.g., rounded or round). A lever arm 406 is connected to the body in cantilever-beam fashion. It is able to flex toward the main body 402 and includes a reduced-width and/or radiused tip 408 configured to push a tooth received in an anchoring head.

The connection 410 between body 402 and lever arm 404 may be configured to serve as a so-called living-hinge. Texture or grip 412 may be provided to indicate desired user thumb position for actuation. The body may be produced in two or more pieces (here with a base part 402A that that also includes cantilever arm 406 and connector 410, and a cover 402B completing the enclosure when assembled). In any case, the parts may be press-fit or snap-fit together, or secured with fasteners. The slider 420 shown is simply snap-fit to the (combined piece) base.

As referenced above, detent features 430 (a second set of such features on the reverse side of the part are hidden in the view) are actuated by sliding a locking collar (the slider) 420 forward. These features comprise a pawl 432 carried on a deflectable beam 434. The pawls 366 are positioned to interact with the spring member 100 to align any of a plurality of windows 130 in the spring member 100 for anchoring tooth 220/220' receipt when the slider 420 is pushed fully forward and the detent(s) are engaged within gaps (G) of the spring member body 100.

The slider 420 may be configured (by selecting material, wall thickness and/or including reinforcement or relief features) to limit the tension on the spring member 100 that can be held by the tensioner 300. By flexing outward, a locked slider will release the detent features(s) if the spring member exceeds a given amount of tension. The limit may be set between about 2 lbf and about 10 lbf or more, or to a limit of 8 lbf, 6 lbf, 4 lbf or between about 2 and 3 lbf, such to about 2.5 lbf or a higher value such as 4 lbf including integral values in increments between about 0.1 and about 0.25 lbf.

Slider 420 includes bosses or wings 422 that may assist advancement. These features are advantageously set in a medial position (as shown) to avoid impingement with or within the surgical pocket (as compared to if they were placed more distally) or interference with hand position if/when directly tensioning the implant spring member body at the proximal end of the medical instrument 400 (should the bosses be placed more proximally) during a medical procedure.

Another option utilizes chuck 440 (shown in the expanded and turned detail illustration) including fore-and-aft locating walls 442, 444 and side-to-side locating ridge, spar or baffle or 446 that interfaces with complementary indexing features (indent surface 254 and nubbins 256 described above) of the crown 250 of the anchoring head crossing tooth piece 220'. The combination of these indexing features may be regarded as providing for proper tooth or cross-pin "clocking" as discussed above with regard to FIGS. 1-6.

With inset 252 capturing ridge 446, the rotational or side-to-side movements of the sliding tooth 220 or 220' is fully constrained in the plane of the anchor 200. Fore-and-aft or forward-and-backward (relative to pocket or socket 350) movement of the cross pin is also limited. However, walls 442 and 444 may be spaced apart (instead of closely capturing shoulders or nubs 256 (which is also an option) to allow for slip across the pocket surface 254 to account for the path of this feature traces through space as beam 406 is deflected to deploy the cross-pin or tooth 200'. As referenced above, similar "chuck" features may be incorporated in or extend from the pusher extension 342 in medical instrument 300.

To summarize these optional features, the sliding tooth may be regarded as including a proximal indexing region formed in a concave shape, and the pusher a complementary region operably engaged with the indexing region whereby rotational or lateral/side-to-side movement of the sliding tooth is blocked. It is also desirable that the complementary region of the pusher also limits fore-to-aft movement of the sliding tooth. As shown, the pusher limits translational movement of the sliding tooth to a prescribed degree (allowing for translation during lever arm actuation) or limit it altogether (so that the sliding tooth might flex during deployment or in connection with a pusher that moves in a purely linear fashion).

In the "clocking function," the socket region of the device may include additional features to set or secure rotational orientation of the anchor 200 received therein. For this purpose, flat interface tips 452 formed in one or more of flexible anchor-holding extensions 454 may interface with complementary flats 246 formed within slot 244 (better seen for the anchor in FIG. 3B). The flat-on-flat interaction prevents rotation of the anchor until release (e.g., as compared to mating circular surface).

These flat-tip features 452 may be used exclusively or in coordination with flattened tip or "nail" sections 456 for relatively longer "fingers" 458 (being longer by virtue of available relief zone 460 adjacent to the face 462 material backing the anchor when loaded onto the instrument) that provide the primary means of flexible release for the anchoring head 200. Otherwise, the longer fingers (two or more) may be configured the same as in the above-referenced '584 application and as in connection with the socket 350 of embodiment 300 above.

Still further, the loader may include a safety lock or tab. This locking member is slidably received in the instrument body to block actuation of the cantilever 406 beam toward an opposing section of the loader body 402 until removed (as shown in FIG. 10). Instrument 400 may include a rear port 464 and guide channel 468 to accommodate the safety tab embodiments shown in FIGS. 11A-11C.

In the first safety tab embodiment 470, finger grip wings 472 connected to cantilever beam sections 474 extending from a slide or bolt section 476. The slide includes a rudder or fin 478 that may be received in slot instrument body channel 468. Received all the way forward through port 464, an optional cradle section 480 may be configured to cradle the anchor cross pin or tooth.

Detent pawls 482 releasably lock the safety tab 470 in front of the connector 410 portions on either side of rear port 464 with the base 484 of each finger grip holding in the rear. To remove the safety lock 470, tabs or wings 472 are squeezed pulling the detents inward and the shaft 476 withdrawn.

Similar action is possible with safety tab 470' or 470" except that these embodiments are simply pulled back to flex the beams and release the detents. Beam sections 486 (in this case simply-supported vs. cantilevered beams) may be relatively thinner than beam sections 474 for increased flexibility in this regard. Anyway, in the case of embodiment 470', an interface tab 490 (or a ring) is pulled. In the case of embodiment 470", a "T" shaped handle 492 user interface is employed. This shape enables a user grip at its (optionally scalloped) sides 494 and additional clearance for spring member tensioning relative to the other embodiments.

Variations

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

Where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein. Moreover, no limitations from the specification are intended to be read into any claims, unless those limitations are expressly included in the claims.

As used herein and in the appended claims, the singular forms "a", "an", and "the" include plural referents unless the context clearly dictates otherwise. In other words, use of the articles allow for "at least one" of the subject items in the description above as well as the claims below. The claims may exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The subject matter described herein and in the accompanying figures is done so with sufficient detail and clarity to permit the inclusion of claims, at any time, in means-plus-function format pursuant to 35 U.S.C. Section 112, Part (f). However, a claim is to be interpreted as invoking this means-plus-function format only if the phrase "means for" is explicitly recited in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, acts, steps, or elements of the embodiments may be recited in or added to the claims, as well as negative limitations that define the inventive scope of the claims by features, functions, acts, steps, or elements that are not within that scope.

The invention claimed is:

1. A system including a medical instrument comprising:
a housing body including a hand grip section and a barrel section;
the housing body receiving a movable trigger section;
a socket located a distal end of the barrel section, the socket configured to hold an anchoring head configured to receive an elongate spring member;
at least one gripper located within the barrel section for grasping the elongate spring member, the at least one gripper configured to hold the elongate spring member upon trigger section compression; and
wherein the medical instrument is configured to tension the elongate spring member by pulling the at least one gripper proximally in response to trigger section compression and hold the tension until release, wherein the anchoring head has a sliding tooth and the system further comprises a button located along the barrel section for pushing the sliding tooth through the anchoring head and across an opening in the elongate spring member.

2. The system of claim 1, wherein the button extends upward from a cantilever beam having a proximal end held in the housing body, and a distal extension of the cantilever beam provides a pusher interface for the sliding tooth of the anchoring head.

3. The system of claim 1, wherein the medical instrument further comprises a tension gauge along a top of the barrel section.

4. The system of claim 1, wherein the medical instrument is further configured to push the at least one gripper inwardly to hold the spring member when the at least one gripper is pulled proximally.

5. The system of claim 1, wherein the medical instrument is configured so that release of tension on the elongate spring member releases the at least one gripper from holding the elongate spring member.

6. The system of claim 1, wherein the medical instrument further comprises a thumb-actuated pawl configured to release tension on the elongate spring member when the pawl is retracted.

7. The system of claim 6, wherein the medical instrument further comprises a trigger pawl connected to the trigger section to advance a ratchet gear also engaged with the thumb-actuated pawl, a pinon gear sharing an axis of rotation and connected to the ratchet gear, and a gear rack connected to the at least one gripper.

8. The system of claim 7, wherein the gear rack is connected to the at least one gripper by a coil spring.

9. The system of claim 8, wherein the at least one gripper is connected to the elongate spring member by a flexible arm.

10. The system of claim 9, having two grippers and two flexible arms.

11. The system of claim 1, further comprising the elongate spring member and the anchoring head, wherein the elongate spring member comprises a plurality of cells.

12. The system of claim 1, wherein the medical instrument is configured so that each successive compression of the trigger section tensions the elongate spring member by one cell.

13. A method of implanting a medical device in a patient's body, the method comprising:
feeding a proximal end of an elongate spring member of an implant into a distal end of a medical instrument and an anchoring head of the implant held by the medical instrument, the elongate spring member comprising a plurality of cells, each cell having an aperture, the anchoring head having a clearance opening; engaging the implant between adjacent cells with at least one gripper upon actuating a tensioning trigger; and
actuating the tensioning trigger until a desired tension reading is displayed by a meter included in the medical instrument.

14. The method of claim 13, wherein the anchoring head further comprises a sliding tooth, and the method further comprises passing the sliding tooth through an aperture in the elongate spring member to secure the tension applied to the elongate spring member.

15. The method of claim 14, wherein the sliding tooth is actuated by a push-button along a top surface of the medical instrument.

16. The method of claim 15, further comprising actuating a release pawl to release tension on a proximal portion of the elongate spring member, thereby releasing the at least one gripper.

17. The method of claim 16, further comprising removing the medical instrument from a body of the implant and trimming any length of the elongate spring member remaining proximal to the anchoring head.

18. The method of claim 13, further comprising:
actuating a release pawl to release tension on a proximal portion of the elongate spring member, thereby releasing the grippers at least one gripper;
re-engaging the implant between adjacent cells with the at least one gripper upon actuating the tensioning trigger; and
re-actuating the tensioning trigger until a second desired tension reading is displayed by the meter.

19. The method of claim 18, wherein the anchoring head further comprises a sliding tooth, and the method further comprises passing the sliding tooth through an aperture in the elongate spring member to secure the tension applied to the elongate spring member.

20. The method of claim 19, wherein the sliding tooth is actuated by a push-button along a top surface of the medical instrument.

21. The method of claim 20, further comprising actuating the release pawl to release tension on a proximal portion of the elongate spring member, thereby releasing the at least one gripper.

22. The method of claim 21, further comprising removing the medical instrument from the body of the implant and trimming any length of the elongate spring member remaining proximal to the anchoring head.

* * * * *